United States Patent
Vess (10) Patent No.: US 9,956,329 B2
(45) Date of Patent: *May 1, 2018

(54) WOUND DRESSING PORT AND ASSOCIATED WOUND DRESSING

(71) Applicant: SMITH & NEPHEW, INC., Memphis, TN (US)

(72) Inventor: Mark A. Vess, Hanson, MA (US)

(73) Assignee: Smith & Nephew, Inc., Memphis, TN (US)

(*) Notice: Subject to any disclaimer, the term of this patent is extended or adjusted under 35 U.S.C. 154(b) by 449 days.

This patent is subject to a terminal disclaimer.

(21) Appl. No.: 14/688,275

(22) Filed: Apr. 16, 2015

(65) Prior Publication Data
US 2015/0314052 A1    Nov. 5, 2015

Related U.S. Application Data

(63) Continuation of application No. 12/044,051, filed on Mar. 7, 2008, now Pat. No. 9,033,942.

(51) Int. Cl.
*A61M 1/00* (2006.01)
*A61F 13/02* (2006.01)
(Continued)

(52) U.S. Cl.
CPC ..... *A61M 1/0088* (2013.01); *A61F 13/00068* (2013.01); *A61F 13/02* (2013.01);
(Continued)

(58) Field of Classification Search
CPC ............ A61F 13/00068; A61F 13/0058; A61F 13/0025; A61F 13/0027; A61F 13/0266;
(Continued)

(56) References Cited

U.S. PATENT DOCUMENTS 1,585,104 A    5/1926  Montgomery
2,736,317 A    2/1956  Alexander
(Continued)

FOREIGN PATENT DOCUMENTS

AU    674837 B2    1/1997
DE    3907007      9/1990
(Continued)

OTHER PUBLICATIONS

US 7,186,244, 03/2007, Hunt et al. (withdrawn)
(Continued)

*Primary Examiner* — Susan Su
(74) *Attorney, Agent, or Firm* — Knobbe, Martens, Olson & Bear, LLP (57) ABSTRACT

A wound dressing for use in a vacuum wound therapy treatment includes a backing layer for positioning over a wound to define a reservoir in which a reduced pressure may be maintained over the wound. A portal member affixed to the backing layer provides a connection to a reduced pressure source through an opening in an ambient surface. A primary port extends between the opening and a primary aperture in a reservoir surface to providing fluid communication between the reservoir and the reduced pressure source. At least one supplemental port establishes fluid communication between the primary port and a supplemental aperture in the reservoir surface that is distinct and substantially spaced from the primary aperture.

18 Claims, 3 Drawing Sheets

(51) Int. Cl.
*A61F 13/00* (2006.01)
*A61M 27/00* (2006.01)

(52) U.S. Cl.
CPC ........ *A61F 13/025* (2013.01); *A61F 13/0206* (2013.01); *A61F 13/0216* (2013.01); *A61F 13/0226* (2013.01); *A61F 13/0266* (2013.01); *A61M 1/0031* (2013.01); *A61F 2013/0028* (2013.01); *A61M 27/00* (2013.01)

(58) Field of Classification Search
CPC ...... A61F 2013/00536; A61F 13/0216; A61M 1/0088
See application file for complete search history.

(56) References Cited

U.S. PATENT DOCUMENTS

| | | |
|---|---|---|
| 3,042,041 A | 7/1962 | Jascalevich |
| 3,568,675 A | 3/1971 | Harvey |
| 3,572,340 A | 3/1971 | Lloyd et al. |
| 3,874,387 A | 4/1975 | Barbieri |
| 3,880,164 A | 4/1975 | Stepno |
| 4,080,970 A | 3/1978 | Miller |
| 4,164,027 A | 8/1979 | Bonnie et al. |
| 4,224,945 A | 9/1980 | Cohen |
| 4,231,357 A | 11/1980 | Hessner |
| 4,261,363 A | 4/1981 | Russo |
| 4,360,015 A | 11/1982 | Mayer |
| 4,382,441 A | 5/1983 | Svedman |
| 4,392,853 A | 7/1983 | Muto |
| 4,468,219 A | 8/1984 | George et al. |
| 4,508,256 A | 4/1985 | Radel et al. |
| 4,540,412 A | 9/1985 | Van Overloop |
| 4,553,967 A | 11/1985 | Ferguson et al. |
| 4,561,435 A | 12/1985 | McKnight et al. |
| 4,569,674 A | 2/1986 | Phillips et al. |
| 4,579,120 A | 4/1986 | MacGregor |
| 4,605,399 A | 8/1986 | Weston et al. |
| 4,614,183 A | 9/1986 | McCracken et al. |
| 4,784,653 A | 11/1988 | Bolton et al. |
| 4,807,625 A | 2/1989 | Singleton |
| 4,906,240 A | 3/1990 | Reed et al. |
| 4,921,492 A | 5/1990 | Schultz et al. |
| 4,941,882 A | 7/1990 | Ward et al. |
| 4,969,880 A | 11/1990 | Zamierowski |
| 4,980,226 A | 12/1990 | Hellgren et al. |
| 5,009,224 A | 4/1991 | Cole |
| 5,056,510 A | 10/1991 | Gilman |
| 5,060,642 A | 10/1991 | Gilman |
| 5,088,483 A | 2/1992 | Heinecke |
| 5,100,395 A | 3/1992 | Rosenberg |
| 5,100,396 A | 3/1992 | Zamierowski |
| 5,106,362 A | 4/1992 | Gilman |
| 5,112,323 A | 5/1992 | Winkler et al. |
| 5,134,007 A | 7/1992 | Reising et al. |
| 5,139,023 A | 8/1992 | Stanley et al. |
| 5,147,698 A | 9/1992 | Cole |
| 5,149,331 A | 9/1992 | Ferdman et al. |
| 5,152,757 A | 10/1992 | Eriksson |
| 5,160,315 A | 11/1992 | Heinecke et al. |
| 5,160,334 A | 11/1992 | Billings et al. |
| 5,176,663 A | 1/1993 | Svedman et al. |
| 5,180,375 A | 1/1993 | Feibus |
| 5,230,496 A | 7/1993 | Shillington et al. |
| 5,244,457 A | 9/1993 | Karami et al. |
| 5,261,893 A | 11/1993 | Zamierowski |
| 5,263,922 A | 11/1993 | Sova et al. |
| 5,300,054 A | 4/1994 | Feist et al. |
| 5,304,161 A | 4/1994 | Noel et al. |
| 5,308,313 A | 5/1994 | Karami et al. |
| 5,358,492 A | 10/1994 | Feibus |
| 5,366,451 A | 11/1994 | Levesque |
| 5,391,161 A | 2/1995 | Hellgren et al. |
| 5,437,651 A | 8/1995 | Todd et al. |
| 5,439,458 A | 8/1995 | Noel et al. |
| 5,447,492 A | 9/1995 | Cartmell et al. |
| 5,486,167 A | 1/1996 | Dragoo et al. |
| 5,520,629 A | 5/1996 | Heinecke et al. |
| 5,525,407 A | 6/1996 | Yang |
| 5,527,293 A | 6/1996 | Zamierowski |
| 5,531,855 A | 7/1996 | Heinecke et al. |
| 5,549,584 A | 8/1996 | Gross |
| 5,593,750 A | 1/1997 | Rothrum et al. |
| 5,599,289 A | 2/1997 | Castellana |
| 5,613,942 A | 3/1997 | Lucast et al. |
| 5,618,278 A | 4/1997 | Rothrum |
| 5,624,423 A | 4/1997 | Anjur et al. |
| 5,636,643 A | 6/1997 | Argenta et al. |
| 5,637,093 A | 6/1997 | Hyman et al. |
| 5,645,081 A | 7/1997 | Argenta et al. |
| 5,678,564 A | 10/1997 | Lawrence et al. |
| 5,695,846 A | 12/1997 | Lange et al. |
| 5,701,917 A | 12/1997 | Khouri |
| 5,738,642 A | 4/1998 | Heinecke et al. |
| 5,795,584 A | 8/1998 | Totakura et al. |
| 5,797,844 A | 8/1998 | Yoshioka et al. |
| 5,797,894 A | 8/1998 | Cadieux et al. |
| 5,894,608 A | 4/1999 | Birbara |
| 5,911,222 A | 6/1999 | Lawrence et al. |
| 5,914,282 A | 6/1999 | Dunshee et al. |
| 5,964,723 A | 10/1999 | Augustine |
| 5,968,001 A | 10/1999 | Freeman |
| 6,071,267 A | 6/2000 | Zamierowski |
| 6,117,111 A | 9/2000 | Fleischmann |
| 6,121,508 A | 9/2000 | Bischof et al. |
| 6,142,982 A | 11/2000 | Hunt et al. |
| 6,169,224 B1 | 1/2001 | Heinecke et al. |
| 6,264,976 B1 | 7/2001 | Heinecke et al. |
| 6,291,050 B1 | 9/2001 | Cree et al. |
| 6,345,623 B1 | 2/2002 | Heaton et al. |
| 6,398,767 B1 | 6/2002 | Fleischmann |
| 6,406,447 B1 | 6/2002 | Thrash et al. |
| 6,420,622 B1 | 7/2002 | Johnston et al. |
| 6,436,432 B2 | 8/2002 | Heinecke et al. |
| 6,458,109 B1 | 10/2002 | Henley et al. |
| 6,461,467 B2 | 10/2002 | Blatchford et al. |
| 6,479,073 B1 | 11/2002 | Lucast et al. |
| 6,553,998 B2 | 4/2003 | Heaton et al. |
| 6,566,575 B1 | 5/2003 | Stickels et al. |
| 6,607,799 B1 | 8/2003 | Heinecke et al. |
| 6,626,891 B2 | 9/2003 | Ohmstede |
| 6,648,862 B2 | 11/2003 | Watson |
| 6,685,681 B2 | 2/2004 | Lockwood et al. |
| 6,685,682 B1 | 2/2004 | Heinecke et al. |
| 6,695,824 B2 | 2/2004 | Howard et al. |
| 6,752,794 B2 | 6/2004 | Lockwood et al. |
| 6,755,807 B2 | 6/2004 | Risk, Jr. et al. |
| 6,800,074 B2 | 10/2004 | Henley et al. |
| 6,814,079 B2 | 11/2004 | Heaton et al. |
| 6,824,533 B2 | 11/2004 | Risk, Jr. et al. |
| 6,838,589 B2 | 1/2005 | Liedtke et al. |
| 6,855,135 B2 | 2/2005 | Lockwood et al. |
| 6,867,342 B2 | 3/2005 | Johnston et al. |
| 6,878,857 B1 | 4/2005 | Chihani et al. |
| 6,903,243 B1 | 6/2005 | Burton |
| 6,936,037 B2 | 8/2005 | Bubb et al. |
| 6,951,553 B2 | 10/2005 | Bubb et al. |
| D515,701 S | 2/2006 | Horhota et al. |
| 6,994,702 B1 | 2/2006 | Johnson |
| 6,994,904 B2 | 2/2006 | Joseph et al. |
| 7,004,915 B2 | 2/2006 | Boynton et al. |
| 7,005,143 B2 | 2/2006 | Abuelyaman et al. |
| 7,070,580 B2 | 7/2006 | Nielsen |
| 7,070,584 B2 | 7/2006 | Johnson et al. |
| 7,108,683 B2 | 9/2006 | Zamierowski |
| 7,117,869 B2 | 10/2006 | Heaton et al. |
| 7,128,735 B2 | 10/2006 | Weston |
| 7,182,758 B2 | 2/2007 | McCraw |
| 7,183,454 B1 | 2/2007 | Rosenberg |
| 7,195,624 B2 | 3/2007 | Lockwood et al. |
| 7,198,046 B1 | 4/2007 | Argenta et al. |
| 7,216,651 B2 | 5/2007 | Argenta et al. |
| 7,273,054 B2 | 9/2007 | Heaton et al. |
| 7,276,247 B2 | 10/2007 | Fansler et al. |

(56) References Cited

U.S. PATENT DOCUMENTS

| | | |
|---|---|---|
| 7,279,612 B1 | 10/2007 | Heaton et al. |
| 7,285,576 B2 | 10/2007 | Hyde et al. |
| 7,316,672 B1 | 1/2008 | Hunt et al. |
| 7,338,482 B2 | 3/2008 | Lockwood et al. |
| 7,381,859 B2 | 6/2008 | Hunt et al. |
| 7,381,860 B2 | 6/2008 | Gudnason et al. |
| 7,438,705 B2 | 10/2008 | Karpowicz et al. |
| 7,442,849 B2 | 10/2008 | Heinecke |
| 7,485,112 B2 | 2/2009 | Karpowicz et al. |
| 7,503,910 B2 | 3/2009 | Adahan |
| 7,524,315 B2 | 4/2009 | Blott et al. |
| 7,531,711 B2 | 5/2009 | Sigurjonsson et al. |
| 7,534,927 B2 | 5/2009 | Lockwood |
| 7,569,742 B2 | 8/2009 | Haggstrom et al. |
| 7,585,554 B2 | 9/2009 | Johnson et al. |
| 7,586,019 B2 | 9/2009 | Oelund et al. |
| 7,608,066 B2 | 10/2009 | Vogel |
| 7,615,036 B2 | 11/2009 | Joshi et al. |
| 7,625,362 B2 | 12/2009 | Boehringer et al. |
| 7,645,269 B2 | 1/2010 | Zamierowski |
| 7,651,484 B2 | 1/2010 | Heaton et al. |
| 7,670,323 B2 | 3/2010 | Hunt et al. |
| 7,678,102 B1 | 3/2010 | Heaton |
| 7,686,785 B2 | 3/2010 | Boehringer et al. |
| 7,699,823 B2 | 4/2010 | Haggstrom et al. |
| 7,699,830 B2 | 4/2010 | Martin |
| 7,723,560 B2 | 5/2010 | Lockwood et al. |
| 7,745,681 B1 | 6/2010 | Ferguson |
| 7,754,937 B2 | 7/2010 | Boehringer et al. |
| 7,758,554 B2 | 7/2010 | Lina et al. |
| 7,759,537 B2 | 7/2010 | Convatec |
| 7,759,539 B2 | 7/2010 | Shaw et al. |
| 7,776,028 B2 | 8/2010 | Miller et al. |
| 7,779,625 B2 | 8/2010 | Joshi et al. |
| 7,781,639 B2 | 8/2010 | Johnston et al. |
| 7,790,945 B1 | 9/2010 | Watson, Jr. et al. |
| 7,790,946 B2 | 9/2010 | Mulligan |
| 7,794,438 B2 | 9/2010 | Henley et al. |
| 7,794,450 B2 | 9/2010 | Blott et al. |
| 7,815,616 B2 | 10/2010 | Boehringer et al. |
| 7,846,141 B2 | 12/2010 | Weston |
| 7,862,718 B2 | 1/2011 | Doyen et al. |
| 7,880,050 B2 | 2/2011 | Robinson et al. |
| 7,883,494 B2 | 2/2011 | Martin |
| 7,896,856 B2 | 3/2011 | Petrosenko et al. |
| 7,896,864 B2 | 3/2011 | Lockwood et al. |
| 7,909,805 B2 | 3/2011 | Weston |
| 7,922,703 B2 | 4/2011 | Riesinger |
| 7,942,866 B2 | 5/2011 | Radl et al. |
| 7,951,124 B2 | 5/2011 | Boehringer et al. |
| 7,964,766 B2 | 6/2011 | Blott et al. |
| 7,976,533 B2 | 6/2011 | Larsson |
| 7,981,098 B2 | 7/2011 | Boehringer et al. |
| 8,002,313 B2 | 8/2011 | Singh et al. |
| 8,021,347 B2 | 9/2011 | Vitaris et al. |
| 8,057,449 B2 | 11/2011 | Sanders et al. |
| 8,061,360 B2 | 11/2011 | Locke et al. |
| 8,062,272 B2 | 11/2011 | Weston |
| 8,083,712 B2 | 12/2011 | Biggie et al. |
| 8,100,887 B2 | 1/2012 | Weston et al. |
| 8,105,295 B2 | 1/2012 | Blott et al. |
| 8,133,211 B2 | 3/2012 | Cavanaugh, II et al. |
| 8,147,468 B2 | 4/2012 | Barta et al. |
| 8,148,595 B2 | 4/2012 | Robinson et al. |
| 8,148,596 B2 | 4/2012 | Miau et al. |
| 8,152,785 B2 | 4/2012 | Vitaris |
| 8,162,907 B2 | 4/2012 | Heagle |
| 8,168,848 B2 | 5/2012 | Lockwood et al. |
| 8,187,237 B2 | 5/2012 | Seegert |
| 8,188,331 B2 | 5/2012 | Barta et al. |
| 8,202,261 B2 | 6/2012 | Kazala, Jr. et al. |
| 8,231,580 B2 | 7/2012 | Hansen et al. |
| 8,235,939 B2 | 8/2012 | Johnson et al. |
| 8,235,955 B2 | 8/2012 | Blott et al. |
| 8,241,261 B2 | 8/2012 | Randolph et al. |
| 8,257,327 B2 | 9/2012 | Blott et al. |
| 8,267,908 B2 | 9/2012 | Coulthard |
| 8,298,200 B2 | 10/2012 | Vess et al. |
| 8,348,910 B2 | 1/2013 | Blott et al. |
| 8,372,049 B2 | 2/2013 | Jaeb et al. |
| 8,376,972 B2 | 2/2013 | Fleischmann |
| 8,430,867 B2 | 4/2013 | Robinson et al. |
| 8,444,612 B2 | 5/2013 | Patel et al. |
| 8,506,554 B2 | 8/2013 | Adahan |
| 8,529,548 B2 | 9/2013 | Blott et al. |
| 8,545,466 B2 | 10/2013 | Andresen et al. |
| 8,641,691 B2 | 2/2014 | Fink |
| 8,734,410 B2 | 5/2014 | Hall et al. |
| 8,771,244 B2 | 7/2014 | Eckstein et al. |
| 8,777,911 B2 | 7/2014 | Heagle et al. |
| 8,784,392 B2 | 7/2014 | Vess et al. |
| 8,801,684 B2 | 8/2014 | Walti et al. |
| 8,814,842 B2 | 8/2014 | Coulthard et al. |
| 8,926,593 B2 | 1/2015 | Croizat et al. |
| 9,227,000 B2 | 1/2016 | Fink et al. |
| 9,452,245 B2 | 9/2016 | Jaeb et al. |
| 2001/0031943 A1 | 10/2001 | Urie |
| 2001/0034223 A1 | 10/2001 | Rieser et al. |
| 2002/0002209 A1 | 1/2002 | Mork |
| 2002/0065494 A1 | 5/2002 | Lockwood et al. |
| 2002/0115952 A1 | 8/2002 | Johnson et al. |
| 2002/0161346 A1 | 10/2002 | Lockwood et al. |
| 2002/0182246 A1 | 12/2002 | Oyaski |
| 2003/0225347 A1 | 12/2003 | Argenta et al. |
| 2004/0039415 A1 | 2/2004 | Zamierowski |
| 2004/0054338 A1 | 3/2004 | Bybordi |
| 2004/0064132 A1 | 4/2004 | Boehringer |
| 2004/0073151 A1 | 4/2004 | Weston |
| 2004/0030304 A1 | 12/2004 | Hunt et al. |
| 2005/0004534 A1 | 1/2005 | Lockwood et al. |
| 2005/0010153 A1 | 1/2005 | Lockwood et al. |
| 2005/0020955 A1 | 1/2005 | Sanders et al. |
| 2005/0065484 A1 | 3/2005 | Watson, Jr. |
| 2005/0070858 A1 | 3/2005 | Lockwood et al. |
| 2005/0085795 A1 | 4/2005 | Lockwood et al. |
| 2005/0101940 A1 | 5/2005 | Radl et al. |
| 2005/0137539 A1 | 6/2005 | Biggie et al. |
| 2005/0203452 A1 | 9/2005 | Weston et al. |
| 2005/0209574 A1 | 9/2005 | Boehringer et al. |
| 2005/0222527 A1 | 10/2005 | Miller et al. |
| 2005/0273066 A1 | 12/2005 | Wittmann |
| 2006/0009744 A1 | 1/2006 | Erdman et al. |
| 2006/0020234 A1 | 1/2006 | Chou et al. |
| 2006/0025727 A1 | 2/2006 | Boehringer et al. |
| 2006/0036221 A1 | 2/2006 | Watson, Jr. |
| 2006/0041247 A1 | 2/2006 | Petrosenko et al. |
| 2006/0079852 A1 | 4/2006 | Bubb et al. |
| 2006/0100586 A1 | 5/2006 | Karpowicz et al. |
| 2006/0155260 A1 | 7/2006 | Blott et al. |
| 2007/0014837 A1 | 1/2007 | Johnson et al. |
| 2007/0016152 A1 | 1/2007 | Karpowicz |
| 2007/0021697 A1 | 1/2007 | Ginther et al. |
| 2007/0032762 A1 | 2/2007 | Vogel |
| 2007/0032778 A1 | 2/2007 | Heaton et al. |
| 2007/0038172 A1 | 2/2007 | Zamierowski |
| 2007/0066946 A1 | 3/2007 | Haggstrom et al. |
| 2007/0156104 A1 | 7/2007 | Lockwood et al. |
| 2007/0167927 A1 | 7/2007 | Hunt et al. |
| 2007/0185426 A1 | 8/2007 | Ambrosio et al. |
| 2007/0185463 A1 | 8/2007 | Mulligan |
| 2007/0219497 A1 | 9/2007 | Johnson et al. |
| 2007/0233022 A1 | 10/2007 | Henley et al. |
| 2007/0265561 A1 | 11/2007 | Yeung |
| 2007/0265585 A1 | 11/2007 | Joshi et al. |
| 2007/0282310 A1 | 12/2007 | Bengtson et al. |
| 2008/0033325 A1 | 2/2008 | Van der Hulst |
| 2008/0039761 A1 | 2/2008 | Heaton et al. |
| 2008/0103489 A1 | 5/2008 | Dahners |
| 2008/0108977 A1 | 5/2008 | Heaton et al. |
| 2008/0119802 A1 | 5/2008 | Reisinger |
| 2008/0161778 A1 | 7/2008 | Steward |
| 2008/0167593 A1 | 7/2008 | Fleischmann |
| 2008/0195017 A1 | 8/2008 | Robinson et al. |
| 2008/0200906 A1 | 8/2008 | Sanders et al. |

(56) References Cited

U.S. PATENT DOCUMENTS

| | | |
|---|---|---|
| 2008/0208147 A1 | 8/2008 | Argenta et al. |
| 2008/0215019 A1 | 9/2008 | Malamutmann |
| 2008/0234641 A1 | 9/2008 | Locke et al. |
| 2008/0243096 A1 | 10/2008 | Svedman |
| 2008/0281281 A1 | 11/2008 | Meyer et al. |
| 2008/0294147 A1 | 11/2008 | Radl et al. |
| 2008/0300578 A1 | 12/2008 | Freedman |
| 2008/0306456 A1 | 12/2008 | Riesinger |
| 2008/0312572 A1 | 12/2008 | Riesinger |
| 2009/0005744 A1 | 1/2009 | Karpowicz et al. |
| 2009/0093778 A1 | 4/2009 | Svedman |
| 2009/0099519 A1 | 4/2009 | Kaplan |
| 2009/0124988 A1 | 5/2009 | Coulthard |
| 2009/0131892 A1 | 5/2009 | Karpowicz et al. |
| 2009/0137973 A1 | 5/2009 | Karpowicz et al. |
| 2009/0157016 A1 | 6/2009 | Carmeli |
| 2009/0171288 A1 | 7/2009 | Wheeler |
| 2009/0192467 A1 | 7/2009 | Hansen et al. |
| 2009/0192499 A1 | 7/2009 | Weston et al. |
| 2009/0227968 A1 | 9/2009 | Vess |
| 2009/0227969 A1 | 9/2009 | Jaeb et al. |
| 2009/0234306 A1 | 9/2009 | Vitaris |
| 2009/0254053 A1 | 10/2009 | Svensby et al. |
| 2009/0293887 A1 | 12/2009 | Wilkes et al. |
| 2009/0299249 A1 | 12/2009 | Wilkes et al. |
| 2009/0299251 A1 | 12/2009 | Buan |
| 2009/0299255 A1 | 12/2009 | Kazala, Jr. et al. |
| 2009/0299257 A1 | 12/2009 | Long et al. |
| 2009/0299303 A1 | 12/2009 | Seegert |
| 2009/0299308 A1 | 12/2009 | Kazala et al. |
| 2009/0299340 A1 | 12/2009 | Kazala et al. |
| 2010/0000524 A1 | 1/2010 | Ohbi |
| 2010/0016767 A1 | 1/2010 | Jones et al. |
| 2010/0036334 A1 | 2/2010 | Heagle et al. |
| 2010/0063464 A1 | 3/2010 | Meyer et al. |
| 2010/0063484 A1 | 3/2010 | Heagle |
| 2010/0069850 A1 | 3/2010 | Fabo |
| 2010/0069858 A1 | 3/2010 | Olson |
| 2010/0069863 A1 | 3/2010 | Olson |
| 2010/0069885 A1 | 3/2010 | Stevenson et al. |
| 2010/0069886 A1 | 3/2010 | Wilkes |
| 2010/0087767 A1 | 4/2010 | McNeil |
| 2010/0094234 A1 | 4/2010 | Ramella et al. |
| 2010/0106106 A1 | 4/2010 | Heaton et al. |
| 2010/0106114 A1 | 4/2010 | Weston et al. |
| 2010/0106188 A1 | 4/2010 | Heaton et al. |
| 2010/0125258 A1 | 5/2010 | Coulthard et al. |
| 2010/0125259 A1 | 5/2010 | Olson |
| 2010/0152639 A1 | 6/2010 | Miau et al. |
| 2010/0160878 A1 | 6/2010 | Hunt et al. |
| 2010/0191198 A1 | 7/2010 | Heagle |
| 2010/0210986 A1 | 8/2010 | Sanders |
| 2010/0262091 A1 | 10/2010 | Larsson |
| 2010/0262094 A1 | 10/2010 | Walton et al. |
| 2010/0262095 A1 | 10/2010 | Hall et al. |
| 2010/0268128 A1 | 10/2010 | Randolph |
| 2010/0305549 A1 | 12/2010 | Miller et al. |
| 2010/0324510 A1 | 12/2010 | Andresen et al. |
| 2010/0324516 A1 | 12/2010 | Braga et al. |
| 2011/0028290 A1 | 2/2011 | Ozawa |
| 2011/0028919 A1 | 2/2011 | Johnnison et al. |
| 2011/0028920 A1 | 2/2011 | Johannison |
| 2011/0125066 A1 | 5/2011 | Robinson et al. |
| 2011/0125110 A1 | 5/2011 | Cotton et al. |
| 2011/0213320 A1 | 9/2011 | Blott et al. |
| 2012/0116334 A1 | 5/2012 | Albert et al. |
| 2012/0143156 A1 | 6/2012 | Bannister et al. |
| 2013/0172835 A1 | 7/2013 | Braga et al. |
| 2013/0172836 A1 | 7/2013 | Vess |
| 2013/0310809 A1 | 11/2013 | Armstrong |
| 2014/0107599 A1 | 4/2014 | Fink et al. |
| 2014/0323997 A1 | 10/2014 | Heagle et al. |
| 2014/0330224 A1 | 11/2014 | Albert et al. |
| 2014/0330225 A1 | 11/2014 | Hall et al. |
| 2014/0330227 A1 | 11/2014 | Coulthard et al. |
| 2015/0018785 A1 | 1/2015 | Vess et al. |

FOREIGN PATENT DOCUMENTS

| | | |
|---|---|---|
| DE | 198 44 355 | 4/2000 |
| DE | 20 2010 009 148 | 10/2010 |
| EP | 0325771 B1 | 9/1993 |
| EP | 0 392 640 B1 | 6/1995 |
| EP | 0 441 418 B1 | 7/1995 |
| EP | 0 751 757 B1 | 1/1997 |
| EP | 0 692 987 | 10/1997 |
| EP | 0 651 983 B1 | 9/1998 |
| EP | 0 777 504 | 10/1998 |
| EP | 0 782 421 | 7/1999 |
| EP | 0 774 242 | 3/2000 |
| EP | 0 690 706 B1 | 11/2000 |
| EP | 1 088 569 | 4/2001 |
| EP | 0 674 892 | 7/2001 |
| EP | 1 129 734 A2 | 9/2001 |
| EP | 0 921 775 B1 | 12/2001 |
| EP | 1 169 071 A1 | 1/2002 |
| EP | 0 948 951 | 6/2002 |
| EP | 0 853 950 | 10/2002 |
| EP | 1 283 702 A1 | 2/2003 |
| EP | 0 729 334 | 3/2003 |
| EP | 0 708 620 | 5/2003 |
| EP | 1 014 905 | 5/2003 |
| EP | 0 993 317 | 9/2003 |
| EP | 0 880 953 | 10/2003 |
| EP | 1 219 311 | 7/2004 |
| EP | 1 018 967 | 8/2004 |
| EP | 1 100 574 | 2/2005 |
| EP | 0 898 471 | 5/2005 |
| EP | 1 556 120 A2 | 7/2005 |
| EP | 1 440 667 | 3/2006 |
| EP | 1 637 088 | 3/2006 |
| EP | 1 284 777 | 4/2006 |
| EP | 1 660 000 A2 | 5/2006 |
| EP | 1 663 062 A2 | 6/2006 |
| EP | 0 982 015 B1 | 8/2006 |
| EP | 1 448 261 | 2/2007 |
| EP | 1 772 160 | 4/2007 |
| EP | 1 227 853 | 1/2008 |
| EP | 1 476 217 | 3/2008 |
| EP | 2 218 431 A2 | 4/2008 |
| EP | 1 920 791 | 5/2008 |
| EP | 1 620 720 | 10/2008 |
| EP | 1 977 776 | 10/2008 |
| EP | 1 986 584 A2 | 11/2008 |
| EP | 1 827 561 | 1/2009 |
| EP | 2 010 065 A1 | 1/2009 |
| EP | 2 127 690 | 2/2009 |
| EP | 2 052 750 | 4/2009 |
| EP | 2 079 507 A2 | 7/2009 |
| EP | 2 081 629 A2 | 7/2009 |
| EP | 2 098 257 | 9/2009 |
| EP | 2 103 290 | 9/2009 |
| EP | 1 513 478 | 12/2009 |
| EP | 2 129 409 A1 | 12/2009 |
| EP | 2 138 139 A2 | 12/2009 |
| EP | 1 652 549 B1 | 1/2010 |
| EP | 1 905 465 | 1/2010 |
| EP | 2 146 759 A1 | 1/2010 |
| EP | 1 314 410 | 2/2010 |
| EP | 2 152 196 A1 | 2/2010 |
| EP | 2 172 164 | 4/2010 |
| EP | 2 203 137 A1 | 7/2010 |
| EP | 2 244 217 A1 | 10/2010 |
| EP | 2 244 746 A2 | 11/2010 |
| EP | 2 254 537 A2 | 12/2010 |
| EP | 2 306 951 A1 | 4/2011 |
| EP | 1 703 922 | 5/2011 |
| EP | 1 517 660 | 8/2011 |
| EP | 1 578 477 B1 | 9/2011 |
| EP | 1 487 389 | 10/2011 |
| EP | 1 169 071 | 2/2012 |
| EP | 2 167 157 | 10/2012 |

(56) References Cited

FOREIGN PATENT DOCUMENTS

| | | |
|---|---|---|
| EP | 2 279 017 | 8/2013 |
| EP | 1 565 219 | 2/2014 |
| EP | 1 906 903 | 4/2014 |
| EP | 1 478 313 | 8/2014 |
| EP | 2 285 430 | 8/2014 |
| EP | 2 109 473 | 11/2014 |
| EP | 2 268 348 | 12/2014 |
| FR | 1163907 | 10/1958 |
| GB | 1 220 857 | 1/1971 |
| GB | 2307180 | 5/1997 |
| GB | 2 307 180 B | 6/2000 |
| GB | 2 336 546 B | 6/2000 |
| GB | 2 344 531 A | 6/2000 |
| GB | 2356148 | 6/2004 |
| GB | 2 415 908 | 1/2006 |
| GB | 2 431 351 A1 | 4/2007 |
| GB | 2431351 | 4/2007 |
| WO | WO 1994/03214 | 2/1994 |
| WO | WO 1994/21207 | 9/1994 |
| WO | WO 1994/23678 | 10/1994 |
| WO | WO 1999/001173 | 1/1999 |
| WO | WO 2000/07653 | 2/2000 |
| WO | WO 2000/61206 | 10/2000 |
| WO | WO 2001/85228 | 11/2001 |
| WO | WO 2001/85248 | 11/2001 |
| WO | WO 2002/043634 | 6/2002 |
| WO | WO 2002/070040 | 9/2002 |
| WO | WO 2002/092783 | 11/2002 |
| WO | WO 2003/086232 | 10/2003 |
| WO | WO 2003/092620 | 11/2003 |
| WO | WO 2003/101508 | 12/2003 |
| WO | WO 2004/018020 | 3/2004 |
| WO | WO 2004/037334 | 5/2004 |
| WO | WO 2004/041064 | 5/2004 |
| WO | WO 2004/060148 | 7/2004 |
| WO | WO 2005/009488 | 2/2005 |
| WO | WO 2005/016179 | 2/2005 |
| WO | WO 2005/025447 | 3/2005 |
| WO | WO 2005/046760 | 5/2005 |
| WO | WO 2005/046761 | 5/2005 |
| WO | WO 2005/046762 | 5/2005 |
| WO | WO 2005/051461 | 6/2005 |
| WO | WO 2005/061025 | 7/2005 |
| WO | WO 2005/072789 | 8/2005 |
| WO | WO 2005/079718 | 9/2005 |
| WO | WO 2005/102415 | 11/2005 |
| WO | WO 2005/105174 | 11/2005 |
| WO | WO 2005/105175 | 11/2005 |
| WO | WO 2005/105176 | 11/2005 |
| WO | WO 2005/105179 | 11/2005 |
| WO | WO 2005/105180 | 11/2005 |
| WO | WO 2005/115497 | 12/2005 |
| WO | WO 2005/115523 | 12/2005 |
| WO | WO 2005/123170 | 12/2005 |
| WO | WO 2006/046060 | 5/2006 |
| WO | WO 2006/052338 | 5/2006 |
| WO | WO 2006/052745 | 5/2006 |
| WO | WO 2006/105892 | 10/2006 |
| WO | WO 2006/114637 | 11/2006 |
| WO | WO 2006/114638 | 11/2006 |
| WO | WO 2006/114648 | 11/2006 |
| WO | WO 2007/006306 | 1/2007 |
| WO | WO 2007/013049 | 2/2007 |
| WO | WO 2007/013064 | 2/2007 |
| WO | WO 2007/015964 | 2/2007 |
| WO | WO 2007/016590 | 2/2007 |
| WO | WO 2007/019038 | 2/2007 |
| WO | WO 2007/030598 | 3/2007 |
| WO | WO 2007/030599 | 3/2007 |
| WO | WO 2007/030601 | 3/2007 |
| WO | WO 2007/031757 | 3/2007 |
| WO | WO 2007/031762 | 3/2007 |
| WO | WO 2007/031765 | 3/2007 |
| WO | WO 2007/041642 | 4/2007 |
| WO | WO 2007/062024 | 5/2007 |
| WO | WO 2007/067685 | 6/2007 |
| WO | WO 2007/084792 | 7/2007 |
| WO | WO 2007/085396 | 8/2007 |
| WO | WO 2007/087808 | 8/2007 |
| WO | WO 2007/087809 | 8/2007 |
| WO | WO 2007/087811 | 8/2007 |
| WO | WO 2007/092397 | 8/2007 |
| WO | WO 2007/095180 | 8/2007 |
| WO | WO 2007/106590 | 9/2007 |
| WO | WO 2007/106591 | 9/2007 |
| WO | WO 2007/106592 | 9/2007 |
| WO | WO 2007/133618 | 11/2007 |
| WO | WO 2007/143060 | 12/2007 |
| WO | WO 2008/008032 | 1/2008 |
| WO | WO 2008/010094 | 1/2008 |
| WO | WO 2008/011774 | 1/2008 |
| WO | WO 2008/012278 | 1/2008 |
| WO | WO 2008/013896 | 1/2008 |
| WO | WO 2008/014358 | 1/2008 |
| WO | WO 2008/016304 | 2/2008 |
| WO | WO 2008/027449 | 3/2008 |
| WO | WO 2008/036162 | 3/2008 |
| WO | WO 2008/040020 | 4/2008 |
| WO | WO 2008/041926 | 4/2008 |
| WO | WO 2008/043067 | 4/2008 |
| WO | WO 2008/048527 | 4/2008 |
| WO | WO 2008/064502 | 6/2008 |
| WO | WO 2008/086397 | 7/2008 |
| WO | WO 2008/100437 | 8/2008 |
| WO | WO 2008/100440 | 8/2008 |
| WO | WO 2008/100446 | 8/2008 |
| WO | WO 2008/112304 | 9/2008 |
| WO | WO 2008/131895 | 11/2008 |
| WO | WO 2008/132215 | 11/2008 |
| WO | WO 2008/135997 | 11/2008 |
| WO | WO 2008/141470 | 11/2008 |
| WO | WO 2008/143628 | 11/2008 |
| WO | WO 2008/154158 | 12/2008 |
| WO | WO 2009/002260 | 12/2008 |
| WO | WO 2009/004370 | 1/2009 |
| WO | WO 2009/016603 | 2/2009 |
| WO | WO 2009/016605 | 2/2009 |
| WO | WO 2009/019229 | 2/2009 |
| WO | WO 2009/021047 | 2/2009 |
| WO | WO 2009/021353 | 2/2009 |
| WO | WO 2009/034322 | 3/2009 |
| WO | WO 2009/062327 | 5/2009 |
| WO | WO 2009/066104 | 5/2009 |
| WO | WO 2009/066106 | 5/2009 |
| WO | WO 2009/067711 | 5/2009 |
| WO | WO 2009/068665 | 6/2009 |
| WO | WO 2009/071926 | 6/2009 |
| WO | WO 2009/071929 | 6/2009 |
| WO | WO 2009/071932 | 6/2009 |
| WO | WO 2009/071933 | 6/2009 |
| WO | WO 2009/071935 | 6/2009 |
| WO | WO 2009/071948 | 6/2009 |
| WO | WO 2009/078790 | 6/2009 |
| WO | WO 2009/086580 | 7/2009 |
| WO | WO 2009/088925 | 7/2009 |
| WO | WO 2009/111655 | 9/2009 |
| WO | WO 2009/114624 | 9/2009 |
| WO | WO 2009/114760 | 9/2009 |
| WO | WO 2009/114786 | 9/2009 |
| WO | WO 2009/114790 | 9/2009 |
| WO | WO 2009/124100 | 10/2009 |
| WO | WO 2009/124473 | 10/2009 |
| WO | WO 2009/124548 | 10/2009 |
| WO | WO 2009/126102 | 10/2009 |
| WO | WO 2009/126103 | 10/2009 |
| WO | WO 2009/137194 | 11/2009 |
| WO | WO 2009/145703 | 12/2009 |
| WO | WO 2009/145894 | 12/2009 |
| WO | WO 2009/158125 | 12/2009 |
| WO | WO 2009/158126 | 12/2009 |
| WO | WO 2009/158127 | 12/2009 |
| WO | WO 2009/158129 | 12/2009 |
| WO | WO 2009/158130 | 12/2009 |
| WO | WO 2010/033271 | 3/2010 |

(56) References Cited

FOREIGN PATENT DOCUMENTS

| WO | WO 2010/033574 | 3/2010 |
|----|----------------|--------|
| WO | WO 2010/033769 | 3/2010 |
| WO | WO 2010/035017 | 4/2010 |
| WO | WO 2010/042240 | 4/2010 |
| WO | WO 2010/051073 | 5/2010 |
| WO | WO 2010/056977 | 5/2010 |
| WO | WO 2010/059712 | 5/2010 |
| WO | WO 2010/059730 | 5/2010 |
| WO | WO 2010/072395 | 7/2010 |
| WO | WO 2010/085270 | 7/2010 |
| WO | WO 2010/094957 | 8/2010 |
| WO | WO 2010/147533 | 12/2010 |
| WO | WO 2010/147592 | 12/2010 |
| WO | WO 2011/115908 | 9/2011 |
| WO | WO 2012/087376 | 6/2012 |

OTHER PUBLICATIONS

U.S. Appl. No. 14/261,296, filed Apr. 24, 2014, Heagle.

Australian Office Action, re AU Applicaton No. 2010341491, dated Dec. 5, 2013.

Chinese Office Action, re CN Application No. 201080064562.2, dated Aug. 27, 2014.

Fleischmann et al., Vacuum Sealing: Indication, Technique, and Results, Eur J Orthop Surg Traumatol, (1995) 5:37-40.

Greer, et al., Techniques for Applying Subatmospheric Pressure Dressing to Wounds in Difficult Regions of Anatomy, JWOCN, vol. 26, Num. 5, 1999 pp. 250-253.

International Preliminary Report on Patentability for PCT/US2010/061938 dated Jun. 26, 2012.

International Search Report and Written Opinion for PCT/US2010/061938 dated Sep. 8, 2011.

International Search Report and Written Opinion for PCT/US2011/041521, dated Oct. 7, 2011.

Jeter, K. "Managing Draining Wounds and Fistulae: New and Established Methods" Chronic Wound Care pp. 240-246, 1990.

KCI V.A.C. Granufoam Bridge Dressing Product Brochure (2009) in 2 pages.

Gorica Zivadinovic, et al., "Vacuum Therapy in the Treatment of Peripheral Blood Vessels," Conference Papers of the 5th Timok Medical Days, Majdanpek, 1986 (161-164).

Health Technology, Literature R., "Vacuum Assisted Closure Therapy for Wound Care", Health Technology Literature Review (Dec. 2004), 3-59.

Kampf, Gunter et al., "Microbicidal Activity of a New Silver-Containing Polymer," SPI-ARGENT II. Sep. 1998, Antimicrobial Agents and Chemotherapy, p. 2440-2442.

WOUND DRESSING PORT AND ASSOCIATED WOUND DRESSING

CROSS-REFERENCE TO RELATED APPLICATIONS

This application is a continuation of U.S. patent application Ser. No. 12/044,051 filed on Mar. 7, 2008, the entirety of which is hereby incorporated by reference.

BACKGROUND

1. Technical Field

The present disclosure relates generally to a wound dressing for treating an open wound with a vacuum wound therapy treatment. In particular, the disclosure relates to a dressing having a portal member providing a connection to a vacuum system such that a reservoir over the wound may be evacuated.

2. Background of Related Art

The body's natural wound healing process is a complex series of events beginning at the moment of injury. Initially the body reacts by delivering proteins and other factors to the wound through the blood stream to minimize the damage. Blood clots to prevent blood loss while cells engulf bacteria and debris to carry it away from the wound site. Next, the body begins to repair itself in a stage of healing often referred to as the proliferative phase. This phase is characterized by the deposition granulation tissue in the wound bed. Granulation tissue provides a base structure over which cells may migrate inwardly from the periphery to close the wound. Finally the process ends as collagen gives strength to new tissue over time often forming a scar.

One technique for promoting the natural healing process, particularly, but not exclusively during the proliferative phase, is known as vacuum wound therapy (VWT). Application of a reduced pressure, e.g. sub-atmospheric, to a localized reservoir over a wound has been found to assist in closing the wound. The reduced pressure may be effective to promote blood flow to the area to stimulate the formation of granulation tissue and the migration of healthy tissue over the wound by the natural process. Also a reduced pressure may assist in removing fluids exuding from the wound, which may inhibit bacterial growth. This technique has proven effective for chronic or non-healing wounds, but has also been used in for other purposes such as post-operative wound care.

The general VWT protocol provides for the introduction of an absorbent filler material, such as non-reticulated foams, non-woven fabrics, or gauze, into the wound to absorb exudates. The wound and the absorbent filler material may then be overlaid by a flexible cover layer such as a polymeric film, for example, to establish a vacuum reservoir over the wound where a reduced pressure may be applied by individual or cyclic evacuation procedures. To allow the reduced pressure to be maintained over time, the cover layer may include an adhesive periphery that forms a substantially fluid tight seal with the healthy skin surrounding the wound.

Although some procedures may employ a micro-pump contained within the vacuum reservoir, most VWT treatments apply a reduced pressure using an external vacuum source. Thus, fluid communication between the vacuum source and the reservoir must be established. To this end, a cover layer will often include a connector or portal member to which air hoses from an external vacuum system may be connected.

An aspect of concern in a VWT treatment is the migration of the filler material and wound exudates in the direction of airflow when the reduced pressure is applied. These substances may be deposited on surfaces within a portal member, for example, and over time cause the obstruction or complete occlusion of these portal members. This phenomenon may limit the level of exudate flow from the wound area, or may even prohibit the application of a reduced pressure to the wound area, thus limiting or defeating the effectiveness of the VWT treatment. Accordingly, a need exists for a dressing suitable for use in a VWT procedure.

SUMMARY

The present disclosure describes a wound dressing for use in a vacuum wound therapy treatment. The wound dressing includes a backing layer for positioning over a wound to define a reservoir in which a reduced pressure may be maintained over the wound. A portal member is affixed to the backing layer such that an ambient surface of the portal member may be fluidly isolated from a reservoir surface of the portal member. The backing layer defines a boundary between the ambient surface and the reservoir surface when the backing layer is positioned over a wound. The portal member comprises a primary port extending between an opening in the ambient surface and a primary aperture in the reservoir surface. The opening is adapted for connection to a suction device and the primary aperture is adapted for establishing fluid communication with the reservoir. The portal member further comprises at least one supplemental port establishing fluid communication between the primary port and a supplemental aperture in the reservoir surface. The supplemental aperture is distinct and substantially spaced from the primary aperture.

The portal member may include a plurality of supplemental ports extending radially outwardly from the primary port. The primary and supplemental apertures may be distributed substantially over the entire reservoir surface. The may be molded from a flexible polymeric or elastomeric material and may include an attachment flange adapted for connection of an adhesively coated film.

The backing layer of the wound dressing may comprise a flexible polymeric membrane. The backing layer may include an adhesive coating adapted to affix the backing layer over the wound and to provide a substantially fluid tight seal around the perimeter of the wound. The adhesive coating may be interrupted such that an intermediate portion of the backing layer remains uncoated.

According to a further aspect of the disclosure, a vacuum wound therapy system includes a contact layer and an absorbent filler positioned in a wound bed, and a portal member affixed to a backing layer positioned over the wound bed to define a vacuum reservoir. The portal member includes a primary port extending between an opening in an ambient surface and a primary aperture in a reservoir surface, and at least one supplemental port extending between the primary port and a supplemental aperture distinct and substantially spaced from the primary aperture.

The contact layer may be formed from a conical apertured film to promote unidirectional flow of exudates from the wound. The absorbent filler material may include a single strand of a polyolefin filament. Also, a vacuum system in fluid communication with the vacuum reservoir may include a vacuum source, a collection canister and a one-way valve.

BRIEF DESCRIPTION OF THE DRAWINGS

The accompanying drawings, which are incorporated in and constitute a part of this specification, illustrate embodiments of the present disclosure and, together with the detailed description of the embodiments given below, serve to explain the principles of the disclosure.

DETAILED DESCRIPTION OF PREFERRED EMBODIMENTS

The wound dressing of the present disclosure promotes healing of a wound by providing a reservoir over the wound where a reduced pressure may be maintained. The reservoir subjects the wound to a sub-atmospheric pressure to effectively draw wound fluid, including liquid exudates, from the wound without the continuous use of a vacuum pump. Hence, vacuum pressure may be applied once, or in varying intervals depending on the nature and severity of the wound. The use of a wound dressing in this manner has been found to promote healing by reducing the probability of infection, stimulating the deposition of granulation tissue and other beneficial processes. The wound dressing of the present disclosure includes a backing layer affixed to a portal member for enhancing the effect of a vacuum wound therapy treatment.

The attached figures illustrate exemplary embodiments of the present disclosure and are referenced to describe the embodiments depicted therein. Hereinafter, the disclosure will be described in detail by explaining the figures wherein like reference numerals represent like parts throughout the several views.

Figure 1:
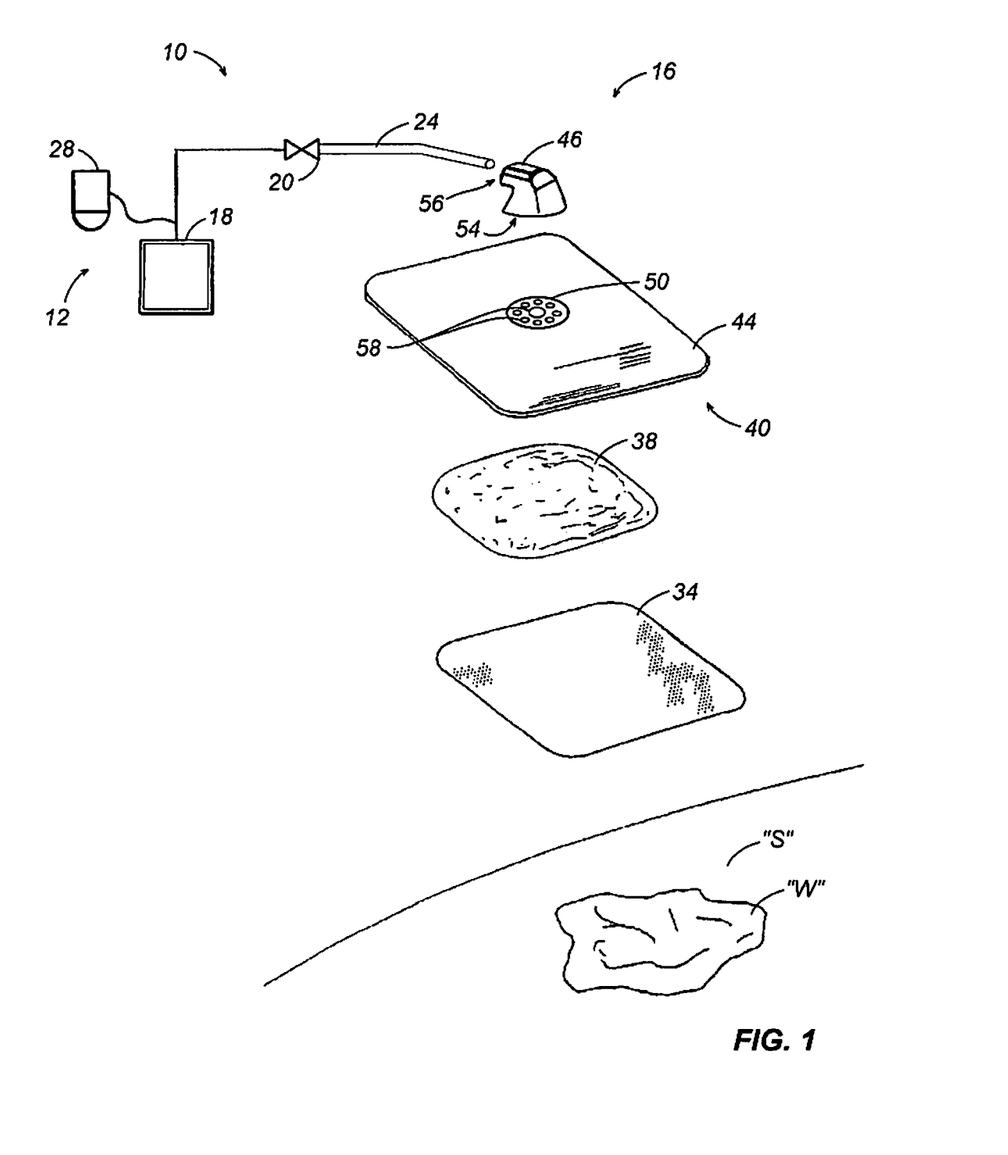
FIG. 1 is an exploded perspective view of a vacuum wound therapy system in accordance with the present disclosure.

Referring initially to FIG. 1, a vacuum wound therapy system according to the present disclosure is depicted generally as 10 for use on a wound "w" surrounded by healthy skin "s." The vacuum wound therapy system 10 includes a vacuum system 12 in fluid communication with a vacuum reservoir 14 (FIG. 4) defined by or within wound dressing 16. The vacuum system 12 includes a vacuum source 18 coupled to the dressing 16 through a one-way valve 20 and a suction device such as vacuum tube 24. A collection canister 28 may be provided for wound drainage and debris. The vacuum system 12 is adapted to provide a reduced pressure to the vacuum reservoir 14 appropriate to stimulate healing of the wound "w." A more detailed description of an appropriate vacuum system 12 is found in commonly assigned U.S. Patent Application Publication 2007/0066946, the entire contents of which are incorporated herein by reference.

Wound dressing 16 generally includes a contact layer 34, filler 38 and a cover layer 40. Cover layer 40 includes a backing layer 44 and a portal member 46. Portal member 46 is configured to establish fluid communication between vacuum reservoir 14 and vacuum system 12 by providing an interface for a suction device such as vacuum tube 24. Each layer of wound dressing 16 is described in greater detail below.

Contact layer 34 may be sufficiently conformable to be positioned in direct contact with an irregularly shaped surface of a wound bed "w." A thin film of polyethylene or other suitable non-adherent material may form the contact layer 34 to limit the adherence of filler 38 and other substances to the wound "w." Apertures or perforations in the film permit fluids to pass through the contact layer 34, allowing for the sub-atmospheric pressure to penetrate into the wound "w" and for exudates to flow freely out of the wound "w." By selecting an appropriate film material, the passage of wound exudate through contact layer 34 may be controlled so as to be substantially unidirectional to prevent wound exudate from flowing back into the wound. To promote a unidirectional flow, a conical apertured film, such as VENTEX™ by Kendall Corp., a division of Covidien, or apertured films by Tredegar Film Products of Richmond, Va., may be selected for forming contact layer 34. Unidirectional flow of exudates may also be promoted by the selection of other materials including a lamination of layers having varying absorptive characteristics. One exemplary material, which may be used as a contact layer is sold under the trademark XEROFLO® by Kendall Corp., a division of Covidien.

Filler 38 may be arranged over contact layer 34 to fill wound "w" to the level of the surrounding healthy skin "s." An absorbent material such as non-woven gauze or reticulated foam may be used for filler 38 to trap any exudate that migrates through contact layer 34. An antimicrobial dressing sold under the trakemark KERLIX® by Kendall Corp., a division of Covidien, may be suitable for use as filler 38. To prevent adhesion to the wound "w," the filler 38 may also comprise a material configured such that any stray fibers do not tend to protrude through apertures of contact layer 34 where they may become engulfed by newly forming granulation tissue. One particular type of material exhibiting this characteristic is often referred to as "tow." The manufacturing process for synthetic fibers often includes an extrusion of an indeterminate length of continuous filaments, which are spun together to form fibers. It is the continuous lengths of un-spun filaments which are referred to as tow. A single length of tow formed from a hydrophobic material such as polyolefin may be laid in the wound bed "w" to form filler 38. This arrangement allows for a complete removal of filler 38 when the dressing 16 is changed without re-injuring the wound "w."

Cover layer 40 may be supplied as a single unit including both backing layer 44 and portal member 46, or alternatively, these items may be provided individually and assembled at the time of installation over the wound "w." Cover layer 40 may be placed over the wound "w" enclosing the contact layer 34 and filler 38 therein.

Backing layer 44 may be formed from a flexible polymeric membrane or film to serve as a fluid barrier to allow for a sub-atmospheric pressure to be established in vacuum reservoir 14, and also as a microbial barrier preventing contaminants from entering the wound area. For example, backing layer 44 may comprise a polyurethane film having a thickness from about 0.8 mils to about 1.0 mils. Preferably, the backing layer 44 is formed from a moisture vapor permeable membrane to promote the exchange of oxygen and moisture vapor between the wound site and the atmosphere. One exemplary material is a transparent membrane sold under the trade name POLYSKIN® II by Kendall Corp., a division of Covidien. Other materials which may be suitable for use in a backing layer include the thin films marketed under the names TEGADERM™ by 3M of St. Paul, Minn. and OPSITE™ by Smith and Nephew PLC of London, UK.

The backing layer 44 of cover layer 40 is adapted to extend laterally beyond the perimeter of the wound bed "w" so as to contact the healthy skin "s" to form a seal thereto. To form the seal, backing layer 44 may be equipped with an adhesive coating on all, or any appropriate portion of a wound facing side. The adhesive coating may comprise, for example, a medical-grade, pressure-sensitive adhesive adapted to provide a fluid-tight and bacteria-tight seal around the wound "w." Thus exudate cannot escape through the edges of the dressing 16 and external air and contaminants may not enter the wound area. To provide such a seal, the adhesive coating may, for example, be in the range from about 1 mil to about 10 mils thick. In general, a high peal-strength adhesive may be used to resist inadvertent lift-off, roll or "flagging," i.e., a failure of the dressing to adhere to itself, at the edges of the cover layer 40. The adhesive may include, for example, those adhesives included with the dressing sold under the trademark ULTEC® Hydrocolloid by Kendall Corp., a division of Covidien.

Figure 4:
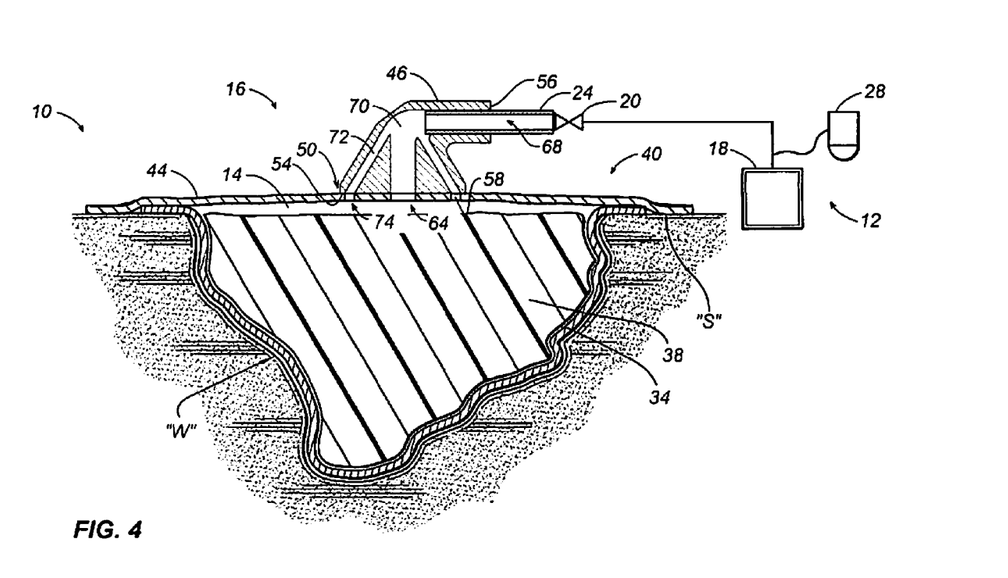
FIG. 4 is a cross sectional view of the vacuum wound therapy system of FIG. 1 installed over wound on a patient.
Figure 5:
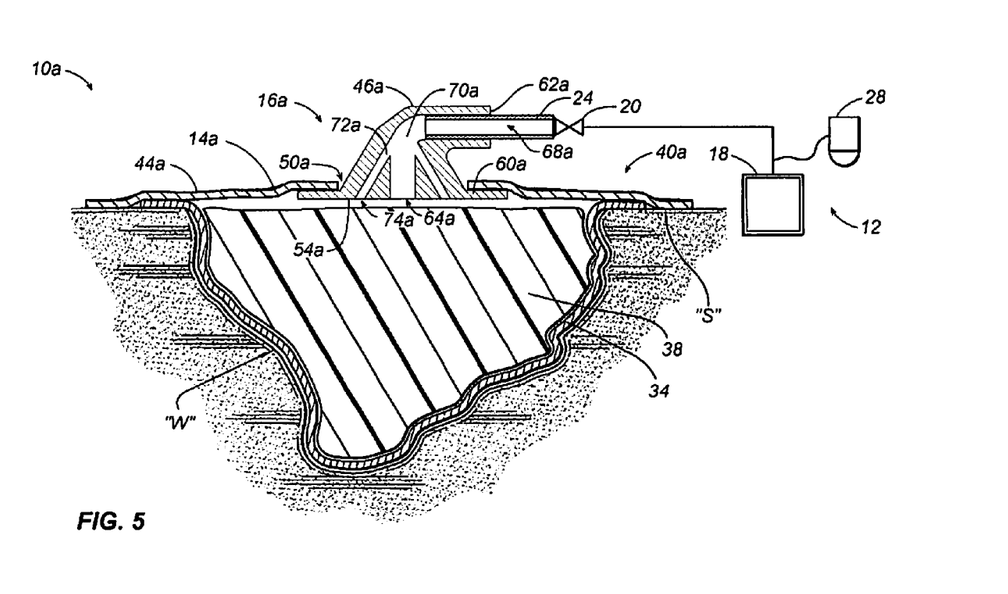
FIG. 5 is a view similar to FIG. 4 depicting an alternate embodiment of a vacuum wound therapy system.

Backing layer 44 includes a connective region 50 to permit of connection of portal member 46. Connective region 50 receives a reservoir surface 54 of portal member 46 to fluidly isolate the reservoir surface 54 from an ambient surface 56 on the portal member 46 except through portal member 46. As illustrated in FIGS. 1 and 4, connective region 50 may be adapted to receive reservoir surface 54 directly such that an adhesive coating on either reservoir surface 54 or connective region 50 affixes the portal member 46 to the backing layer 44. Backing layer 44 defines a boundary between reservoir surface 54 and ambient surface 56. This arrangement permits isolation of reservoir surface 54 from reservoir 14, i.e. reservoir surface 54 may be disposed outside of reservoir 14. Perforations 58 may be formed through the connective region 50 to permit fluids to be drawn from reservoir 14. Alternatively, as illustrated in FIG. 5, backing layer 44a may include an entry 50a dimensioned such that a portion of portal member 46a protrudes through backing layer 44a. An appropriately positioned adhesive coating may form a seal between a wound facing side of backing layer 44a and an oppositely oriented surface of a flange 60a. This arrangement permits reservoir surface 54a to be positioned within reservoir 14a fluidly isolating reservoir surface 54a from ambient surface 56a. Other arrangements are contemplated for affixing a portal member 46, 46a to a backing layer 44, 44a, which may include other parts such as sealing rings (not shown).

Backing layer 44 may include an interrupted adhesive coating such that only the portions of backing layer 44 forming a seal are coated. For example, backing layer 44 may include a band of adhesive coating around the periphery to form a seal with the skin "s," and another band near the connective region 50 to form a seal with the portal member 46. An intermediate portion of backing layer 44 may remain uncoated to limit the adherence of backing layer 44 to the filler 38, contact layer 34 or other surfaces. Such an arrangement may facilitate removal of the dressing 16 without re-injuring the wound "w."

Figure 2:
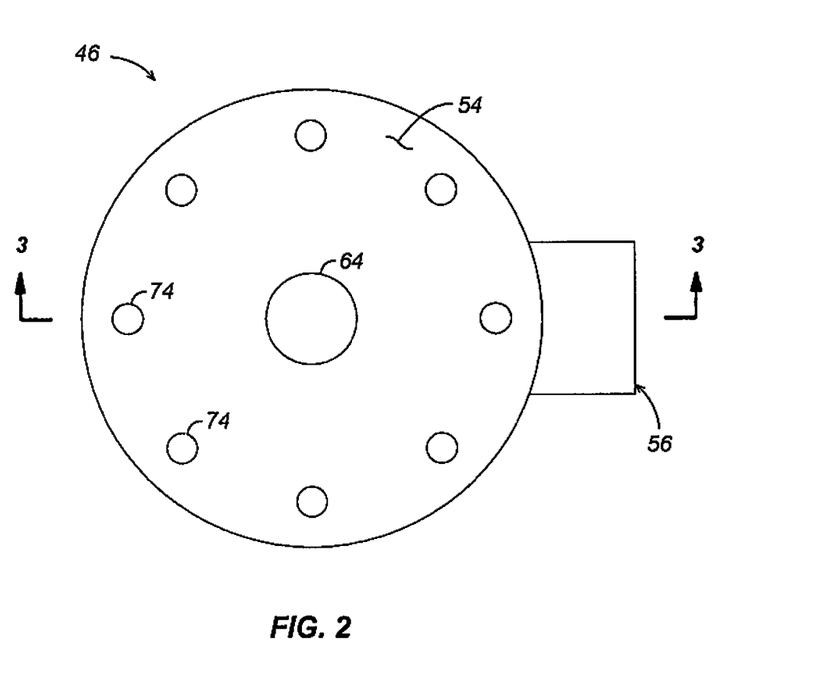
FIG. 2 is an orthographic view of a wound facing side of the portal member of FIG. 1.
Figure 3:
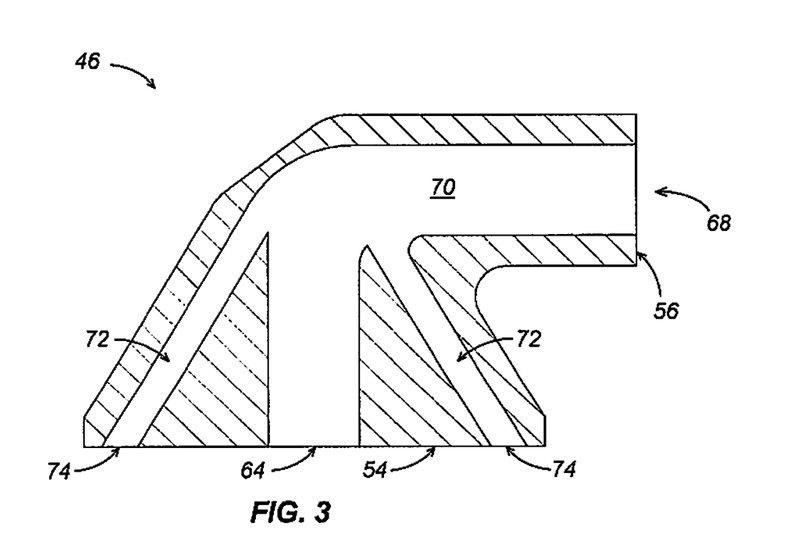
FIG. 3 is a cross sectional view taken along the line 3-3 of FIG. 2.

Referring now to FIGS. 2 and 3, a portal member 46 may be formed as a rigid component, or alternatively portal member 46 may be molded from a flexible polymeric or elastomeric material. Flexibility in portal member 46 facilitates the placement of wound dressing 16 on curved areas of a patient's skin "s." Portal member 46 includes a reservoir surface 54 and an ambient surface 56. The reservoir surface 54 is adapted to be positioned such that a primary aperture 64 therein may fluidly communicate with vacuum reservoir 14, through a perforation 58 for example. Ambient surface 56 may be positioned in the environment surrounding dressing 16 and includes an opening 68 adapted for connection to a suction device such as vacuum tube 24 of vacuum system 12. A primary port 70 is defined between the primary aperture 64 and the opening 68 to permit fluid communication between the reservoir 14 and the vacuum system 12.

Branching from primary port 70 is a radial array of supplemental ports 72 extending to reservoir surface 54. Each of the supplemental ports 72 terminates at a supplemental aperture 74 distinct from and substantially spaced from primary aperture 64. Any number, distribution and arrangement of supplemental ports 72 may be included to distribute supplemental openings 74 over the reservoir surface 54. As FIG. 2 illustrates supplemental apertures 74 may be positioned near a periphery of reservoir surface 54 such that fluids may be drawn from reservoir 14 over a collection area spanning the entire area covered by the portal member 46. Any number, size and arrangement of primary and supplemental apertures 64, 74 is contemplated to effectively draw fluids for a particular application.

Referring now to FIG. 4, wound dressing 16 may be installed on a patient to cover a wound "w." Reservoir 14 is defined by or within wound dressing 16 when applied to the skin "s." Contact layer 34 is positioned in direct contact with the wound "w" and filler 38 is positioned up to the level of healthy skin "s." Portal member 46 may be positioned over connective region 50 of backing layer 44 such that the primary and supplemental apertures 64, 74 are aligned with perforations 58. This will allow fluids to be drawn into primary and supplemental ports 70, 72 from reservoir 14. Ambient surface 56 is fluidly isolated from reservoir 14 except through primary and supplemental ports 70, 72. Opening 68 in the ambient surface 56 receives vacuum tube 24, thus fluidly connecting vacuum system 12 with reservoir 14.

Evacuating the reservoir 14 may impart a tendency for filler material 38 and wound exudate to migrate in the direction of airflow. This tendency for migration may result in the obstruction or occlusion of one or more of the primary and supplemental ports 70, 72. However, because portal member 46 may include many apertures 64, 74 distributed over the entire area covered by the portal member 46, the effectiveness of the VWT procedure may persist. If one of the apertures 64, 74 becomes clogged, fluids will be drawn to another one of the apertures 64, 74 that is distinct and substantially spaced from the clogged aperture 64, 74.

Referring now to FIG. 5, an alternate embodiment of a vacuum wound therapy system is depicted generally as 10a. Wound dressing 16a includes a portal member 46a protruding through entry 50a of cover layer 40a. Backing layer 44a adheres to the flange 60a of the portal member 46a and also to the skin "s" such that the reservoir surface 54a and ambient surface 56a are fluidly isolated except through the primary and supplemental ports 70a, 72a. Ambient surface 56a has an opening 68a therein for connection of a suction device such as vacuum tube 24. Fluid communication is thus established between reservoir 14a and vacuum system 12 through primary port 70a, and primary opening 64a. Supplemental ports 72a establish fluid communication between primary port 70a and supplemental apertures 74a in reservoir surface 54a. Supplemental apertures 74a are distinct and substantially spaced from primary aperture 64a. In this arrangement, reservoir surface 54a is enclosed by reservoir 14a.

Portal member 46a includes a radial array of supplemental ports 72a such that apertures 64a, 74a may be distributed substantially over the entire reservoir surface 54a. This arrangement provides a means of keeping a collection area of the port 46a exposed to as much of the dressing 16a as possible.

Although the foregoing disclosure has been described in some detail by way of illustration and example, for purposes of clarity or understanding, it will be obvious that certain changes and modifications may be practiced within the scope of the appended claims.

What is claimed is:

1. A negative pressure wound therapy dressing comprising:
   a backing layer configured to be placed over a wound; and
   a port having a wound-facing surface and configured to be affixed to the backing layer, the port comprising:
      an opening configured to be in fluidic communication with a source of negative pressure;
      a primary aperture configured to be in fluidic communication with the wound, the primary aperture positioned on the wound-facing surface;
      a primary port extending between the opening and the primary aperture, the primary port configured to communicate negative pressure from the source of negative pressure to the wound;
      a plurality of supplemental ports in fluidic communication with the primary port and a plurality of supplemental apertures positioned on the wound-facing surface and configured to be in fluidic communication with the wound, wherein the plurality of supplemental apertures surround the primary aperture and are distributed over the wound-facing surface such that a first supplemental aperture is not collinear with a second and third supplemental aperture of the plurality of supplemental apertures.

2. The wound dressing according to claim 1, wherein the port is molded from flexible polymer.

3. The wound dressing according to claim 1, wherein the port further comprises an attachment flange adapted for connection to the backing layer.

4. The wound dressing according to claim 1, wherein the backing layer comprises a flexible polymeric membrane.

5. The wound dressing according to claim 1, wherein the backing layer is configured to form a substantially fluid tight seal around a perimeter of a wound to define a reservoir configured to maintain negative pressure.

6. The wound dressing according to claim 1, wherein the backing layer comprises an adhesive coating around a periphery thereof, the adhesive coating adapted to affix the backing layer over the wound and to provide a substantially fluid tight seal around the perimeter of the wound.

7. The wound dressing according to claim 6, wherein the adhesive coating is interrupted such that an intermediate portion of the backing layer remains uncoated.

8. The wound dressing according to claim 1, wherein the supplemental apertures are distinct and spaced from the primary aperture.

9. The wound dressing according to claim 1, wherein the port is pre-affixed to the backing layer.

10. The wound dressing according to claim 1, further comprising a wound contact layer configured to be positioned in direct contact with the wound, the wound contact layer configured to permit substantially unidirectional fluid flow so that exudate removed from the wound is prevented from flowing back into the wound.

11. A vacuum wound therapy system comprising:
    a wound contact layer configured to be positioned in direct contact with a wound, the wound contact layer configured to permit substantially unidirectional fluid flow so that exudate removed from the wound is prevented from flowing back into the wound;
    an absorbent filler overlying the wound contact layer;
    a backing layer overlying the absorbent filler and configured to be positioned over the wound to define a vacuum reservoir over the wound; and
    a port having a wound-facing surface and configured to be affixed to the backing layer outside the vacuum reservoir, the port comprising:
       an opening configured to be in fluidic communication with a source of negative pressure;
       a primary aperture configured to be in fluidic communication with the wound, the primary aperture positioned on the wound-facing surface;
       a primary port extending between the opening and the primary aperture, the primary port configured to communicate negative pressure from the source of negative pressure to the wound;
       a plurality of supplemental ports in fluidic communication with the primary port and a plurality of supplemental apertures positioned on the wound-facing surface and configured to be in fluidic communication with the wound, wherein the plurality of supplemental apertures surround the primary aperture and are distributed over the wound-facing surface such that a first supplemental aperture is not collinear with a second and third supplemental aperture of the plurality of supplemental apertures.

12. The vacuum wound therapy system according to claim 11, wherein the absorbent filler comprises a non-reticulated foam, non-woven fabric, or gauze.

13. The vacuum wound therapy system according to claim 11, further comprising a vacuum system in fluid communication with the vacuum reservoir.

14. The vacuum wound therapy system according to claim 13, wherein the vacuum system includes a vacuum source, a collection canister and a one-way valve.

15. The vacuum wound therapy system according to claim 11, wherein the supplemental apertures are distinct and spaced from the primary aperture.

16. The vacuum wound therapy system according to claim 11, wherein the primary aperture and the plurality of supplemental apertures are positioned over the absorbent filler.

17. The vacuum wound therapy system according to claim 11, wherein the port further comprises an attachment flange adapted for connection to the backing layer.

18. The vacuum wound therapy system according to claim 11, wherein the port is pre-affixed to the backing layer.

* * * * *